United States Patent
Grimberg et al.

(10) Patent No.: US 10,466,258 B2
(45) Date of Patent: Nov. 5, 2019

(54) DEVICE AND PROCESS FOR SAMPLE PREPARATION

(71) Applicant: Omrix Biopharmaceuticals Ltd., Rehovot (IL)

(72) Inventors: Elena Grimberg, Rehovot (IL); Roberto Meidler, Rehovot (IL); Yonit Tiberman, Nes Ziona (IL); Nadav Orr, Mazkeret Batia (IL); Nadav Ashkenazy, Tel Aviv (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 173 days.

(21) Appl. No.: 15/477,692

(22) Filed: Apr. 3, 2017

(65) Prior Publication Data

US 2017/0285047 A1 Oct. 5, 2017

Related U.S. Application Data

(60) Provisional application No. 62/318,315, filed on Apr. 5, 2016.

(51) Int. Cl.
| | |
|---|---|
| *B01D 61/18* | (2006.01) |
| *B01L 3/00* | (2006.01) |
| *C12Q 1/56* | (2006.01) |
| *G01N 33/86* | (2006.01) |

(52) U.S. Cl.
CPC ............. *G01N 33/86* (2013.01); *B01D 61/18* (2013.01); *B01L 3/502* (2013.01); *C12Q 1/56* (2013.01); *B01D 2325/38* (2013.01); *B01L 2300/0681* (2013.01); *B01L 2300/0829* (2013.01)

(58) Field of Classification Search
CPC ........ B01D 61/18; B01D 61/02; B01D 61/00; B01L 3/502; B01L 3/50; B01L 3/00; C12Q 1/56; C12Q 1/00
USPC ..................................................... 422/500, 50
See application file for complete search history.

(56) References Cited

U.S. PATENT DOCUMENTS 6,159,368 A * 12/2000 Moring ................. B01D 61/18
                                                         210/258
2006/0019410 A1    1/2006 St. Claire, III

FOREIGN PATENT DOCUMENTS

EP          0415983       11/1989
WO     WO 2013/098805      7/2013

OTHER PUBLICATIONS

Dempfle et. al. 'A 96-well microfiltration assay for measurement of Total Clottable Fibrinogen' Thromb Haemost, 1999, 81, 264-267.
(Continued)

*Primary Examiner* — Christine T Mui
(74) *Attorney, Agent, or Firm* — David R. Crichton

(57) ABSTRACT

Provided is a method, device and system for an in-situ preparation of a sample, for example, for use in detecting the presence of, and/or quantifying, clottable fibrinogen in such a sample.

14 Claims, 7 Drawing Sheets

(56) References Cited

OTHER PUBLICATIONS

Gaffney P.J. and Wong M.Y. 'Collaborative study of a proposed International Standard for plasma Fibrinogen measurement.' Thrombosis and Heamostasis, 68 (4), pp. 428-432, 1992.
Dudek, M.M. et al 'Development of a Point of Care Lateral Flow Device for Measuring Human Plasma Fibrinogen' Analytical Chemistry vol. 82, No. 5 (2010) pp. 2029-2035.
Millipore Corporation: 'Multiscreen 96-well plates' in 'User Guide Multiscreen 96-well plates' (2013) EMD Millipore Corporation pp. 1-4.
International Search Report re: PCT/IL2017/000002 dated Jul. 18, 2017.

* cited by examiner

DEVICE AND PROCESS FOR SAMPLE PREPARATION

CROSS-REFERENCE TO RELATED APPLICATIONS

This application claims the benefit of U.S. provisional application 62/318,315 filed on Apr. 5, 2016.

TECHNOLOGICAL FIELD

The presently disclosed subject matter refers to an in-situ preparation of a sample, for example, for use in detecting the presence of, and/or quantifying, clottable fibrinogen in such a sample.

BACKGROUND

Clottable fibrinogen needs to be detected and quantified e.g. when producing fibrinogen based products, such as fibrinogen concentrate and fibrin sealants.

The presently disclosed subject matter particularly refers to the preparation of a sample for the detection of clottable fibrinogen by so-called gravimetric assay process according to the European Pharmacopeia 7.0 (also see: Gaffney P. J. and Wong M. Y. Collaborative study of a proposed International Standard for plasma Fibrinogen measurement. Thrombosis and Heamostasis, 68 (4), pp. 428-432, 1992), the process generally including the following steps:
a) adding thrombin solution and EDTA to the tested fibrinogen containing sample, thereby forming a fibrin clot. EDTA (a $Ca^{++}$ chelator agent) inhibits the activation of FXIII by thrombin to FXIIIa (plasma-transglutaminase), thus preventing the formation of $\gamma$-glutamyl-$\epsilon$-lysine bridge of non-clottable protein to fibrin;
b) drying the formed clot (e.g. by absorption of the liquid on a Whatman paper) followed by several washes e.g. with a saline solution whereby "non-clottable" proteins are removed; and
c) having the remained fibrin clot following step (b) degraded (e.g. by sulfuric acidic, or a mixture of 6M urea and 0.2M NaOH), thereby producing a sample for further use in detection/quantification of fibrinogen therein by any known method e.g. a spectrophotometer measurement.

Dempfle et. al. ("A 96-well microfiltration assay for measurement of Total Clottable Fibrinogen"; Thromb Haemost, 1999, 81, 264-267) discloses a gravimetric assay process generally including the following steps:
a) adding thrombin solution to a fibrinogen containing sample disposed on a filtration membrane, in order to form a fibrin clot on that membrane;
b) washing the clot formed on the filtration membrane in step (a) and drying it by applying vacuum to the membrane at its side opposite to that holding the fibrin clot, whereby "non-clottable" proteins are removed through the filtration membrane, leaving thereon dried clottable fibrin; and
c) dissolving the fibrin clot remained in step (b) in solvent solution, producing thereby the sample for its further use in detection/quantification of fibrinogen therein by any known method.

In Dempfle et. al. a 96-well microfiltration assay is used, wherein each well comprises a 1.2 μm pore size hydrophilic membrane, preconditioned with a detergent. In this process, steps (a) and (b) above are performed within the array, whilst after step (b) the membranes with fibrin clot adhered thereto are removed from the assay, and the solubilization of the fibrin clot from each of the 96 membranes (step (c) above) is performed in a separate test tube, one membrane with adherent fibrin clot per such tube.

GENERAL DESCRIPTION

According to one aspect of the presently disclosed subject matter, there is provided a device for performing an in-situ preparation of a sample, said preparation comprising a number of steps and involving at least two substances, the device comprising:
  a substance receiving portion having a top and a bottom and having dimensions sufficient to receive therein through the top a predetermined amount of material required for each of said steps;
  a membrane having an upper surface constituting the bottom of the substance receiving portion and facing towards an interior of the substance receiving portion, and a lower surface facing towards an exterior of the substance receiving portion, and having such a structure as to allow fluid disposed in the substance receiving portion at least in one of the steps, to be transferred therefrom through the membrane towards the exterior of the substance receiving portion only when vacuum is applied to its outer surface; and
  at least one blocking member, said member being configured for taking one position, in which it is disposed in close proximity to the outer surface of the membrane and covers it so as to prevent the possibility of fluid communication between the substance receiving portion and the exterior of the substance receiving portion through the membrane, and another position spaced from the membrane, so as to allow said fluid communication.

The above structure of the device and, particularly, the fact that it includes the blocking member, allows performing therein all the steps of the gravimetric assay process of preparation of a sample for the detection of clottable fibrinogen. In particular, with the above structure, the solubilization of the fibrin clot can be performed in the same cavity of the device, where the clot has been formed, washed and dried.

The device can comprise an elongated cavity with upper and lower openings and a first cavity portion constituted by said substance receiving portion extending between the upper opening and the membrane, and a second cavity portion extending between said membrane and the lower opening of the cavity, and wherein said blocking member is insertable into the second cavity portion from the lower opening of the device.

In order for the membrane to allow fluid to be transferred from its one side to its other side when vacuum is applied thereto, the membrane can be made of a porous material. When the device is to be used for sample preparation for detecting the presence and/or quantifying fibrinogen, superior performance of the device can be expected with the membrane having pores of a size in the range of 10 to 40 μm, more particularly, in the range of 20 to 30 μm, and still more particularly, about 25 μm.

The material, from which the membrane is made, can further be free of absorption properties, and can be inert at least with respect to said substances. Furthermore, the material can be hydrophobic to prevent the substance required to form the fibrin clot from spreading on the membrane and thus covering the majority of the surface of the membrane, thereby blocking the pores.

The blocking member can have an extension along the axis of the elongated cavity, which is at least not less than the corresponding extension of the second cavity portion. This structure, when the blocking member is disposed in close proximity to the membrane, further prevents the possibility of fluid communication between the substance receiving portion and the second open end through the membrane.

The above device can comprise a plurality of the elongated cavities or substance receiving portions, constituting an array of wells, and a corresponding plurality of blocking members, if any, each configured for taking positions relative to the corresponding cavity or substance receiving portions.

In accordance with a further aspect of the presently disclosed subject matter, there is provided a device for performing an in-situ preparation of a sample, said preparation comprising a number of steps and involving at least two substances, the device comprising:
  at least one substance receiving portion having a top and a bottom and having dimensions sufficient to receive therein through the top a predetermined amount of material required for each of said steps; and
  a membrane having an upper surface constituting the bottom of the substance receiving portion and facing towards an interior of the substance receiving portion, and a lower surface facing towards an exterior of the substance receiving portion, and having such a structure as to allow fluid disposed in the substance receiving portion at least in one of the steps, to be transferred therefrom to the exterior of the substance receiving portion through the membrane only when vacuum is applied to its lower surface;
wherein the membrane is made of a hydrophobic material, which is free of absorption properties at least with respect to said substances thereby allowing a clot formed thereon in the substance receiving portion by mixing said substances and, optionally, incubating the mixture in the cavity, to cover the membrane only partially.

In particular, the hydrophobic material can be selected such relative to the substances used that the clot occupies an area on the membrane that does not exceed 80% of the area of the membrane at the bottom of the substance receiving portion. More particularly, the area occupied by the clot can be in the range of between 50% and 80% of the area of the membrane at the bottom of the substance receiving portion.

The use of porous membranes is known, for example, from US 2006/0019410 and EP 0415983, which disclose placing on one side of a porous membrane a fluid mixture and transferring to its other side a part of the mixture, for further use thereof in a detecting/quantifying process. US 2006/0019410 further discloses applying vacuum to the latter side of the membrane and the possibility for the membrane to have hydrophobic properties. However, processes described in these publications do not use the hydrophobic properties of the membrane in the manner as in the presently disclosed subject matter.

The device of any of the above aspects can constitute a part of a system comprising:
  an upper plate having an upper surface, a lower surface and a plurality of first well portions extending therebetween, each having an upper open end at the upper surface and a lower open end at the lower surface, each first well portion constituting said substance receiving portion; and
  a membrane sheet configured to be assembled with the upper plate at its lower surface so that an area of the membrane closest to the lower open end of each first well portion and corresponding thereto in shape and dimension constitutes a bottom of the first well portion.

The system can further comprise a lower plate having an upper surface, a lower surface and a plurality of second well portions extending therebetween and having cross-sectional shape and dimension corresponding to those of the first well portions, each second well portion having an upper open end at the upper surface of the lower plate and a lower open end at the lower surface of the lower plate; the upper and lower plates being configured for securing to each other with the membrane sandwiched therebetween so that each pair of corresponding first and the second well portions is coaxially aligned to form one well and are separated by said area of the membrane.

The system can further comprise a sealing arrangement for forming a seal around the above area of the membrane and the corresponding lower open end of the first well portion, and/or the corresponding upper open end of the second well portion, for preventing leakage of fluid from the well into spaces between the plates and the membrane.

The system can comprise locks for securely holding together the above plates, the membrane and the upper and lower sealing sheets forming thereby an assembly with open-ended wells. Alternatively, the system can comprise bolts and nuts for this purpose.

The system can further comprise a blocking base with said blocking members each having a blocking surface corresponding in shape and dimension to said area of the membrane. The blocking members can be in the form of a plurality of posts protruding from the blocking base's upper surface, said blocking surfaces being constituted by top flanges of the posts. These blocking posts can cover the membrane, when brought into close proximity thereto, to prevent the possibility of fluid communication between the first and second well portions through the membrane.

The system can comprise locks for securely holding the blocking base in fixed relation relative to the upper and lower plates, when the blocking members are in close proximity to the membrane.

The assembly can be configured for mounting on a vacuum manifold so that the lower open ends of the second well portions are exposed for applying vacuum thereto, when said blocking members are away from the membrane.

In accordance with other aspects of the presently disclosed subject matter, there is provided an in-situ process of sample preparation for detecting the presence and/or quantifying fibrinogen, using any of the devices as described above, the process comprising a number of steps and involving at least two substances, one of which comprises fibrinogen and the other one comprises a proteolytic enzyme, which is capable of forming fibrin when it reacts with fibrinogen e.g. thrombin. These steps include at least the following:
  (a) forming a clot by mixing said at least two substances on the membrane in the substance receiving portion, and optionally incubating the mixture;
  (b) washing the clot with a liquid in the substance receiving portion;
  (c) removing the liquid by applying vacuum at the lower opening of the cavity, thereby withdrawing the liquid from the substance receiving portion through the membrane via the second open end;
  (d) optionally, repeating steps (b) and (c) a number of times, said number optionally not exceeding 10;

(e) preventing fluid communication between the substance receiving portion and lower open end through the membrane; and.

(f) solubilizing the clot in the substance receiving portion with a suitable aqueous solution.

In some embodiments, steps (a) to (f) are carried out in-situ or in the same substance receiving portion, cavity portion and/or well.

The aqueous solution can comprise alkaline substance, e.g. NaOH, and/or chaotropic agent, e.g. Urea or Guanidine Hydrochloride.

In accordance with, yet, another aspect of the presently disclosed subject matter, there is provided a kit for assembling a system as described above. In particular, with the system comprising an array of wells, each having the form of an elongated cavity extending between a first well open end and a second well open end, the kit comprises:

an upper plate having an upper surface, a lower surface and a plurality of first well portions extending therebetween, each having an upper open end at the upper surface and a lower open end at the lower surface, the upper end constituting the first well open end;

a membrane sheet configured to be assembled with the upper plate at its lower surface so that an area of the membrane closest to the lower open end of each first well portion and corresponding thereto in shape and dimension, constitutes a bottom of the first well portion; and a lower plate having an upper surface, a lower surface and a plurality of second well portions extending therebetween and having cross-sectional shape and dimension corresponding to those of the first well portions, each second well portion having an upper open end at the upper surface of the lower plate and a lower open end at the lower surface of the lower plate;

wherein the upper and lower plates are configured for being fixed to each other with the membrane sandwiched therebetween so that the first and the second well portions are coaxially aligned to form said well and are separated by said area of the membrane, the lower end of each second well portion constituting the second well open end.

In one aspect, the invention provides a device for performing an in-situ preparation of a sample, said preparation comprising a number of steps and involving at least two substances, the device comprising:

a substance receiving portion (41) having a top (11) and a bottom and having dimensions sufficient to receive therein through the top (11) a predetermined amount of material required for each of said steps;

a membrane (30) having an upper surface (31a) constituting the bottom of the substance receiving portion (41) and facing towards an interior of the substance receiving portion, and a lower surface (31b) facing towards an exterior of the substance receiving portion, and having such a structure as to allow fluid disposed in the substance receiving portion at least in one of the steps, to be transferred therefrom through the membrane towards the exterior of the substance receiving portion only when vacuum is applied to its bottom; and at least one blocking member (51), said member being configured for taking one position, in which it is disposed in close proximity to the lower surface of the membrane and covers it so as to prevent the possibility of fluid communication between the substance receiving portion and the exterior of the substance receiving portion through the membrane, and another position spaced away from the membrane, so as to allow said fluid communication when vacuum is applied to the bottom of the substance receiving portion.

In one embodiment of the present invention, the device further comprises an elongated cavity (40) with upper and lower openings (11, 21), a first cavity portion constituted by said substance receiving portion (41), and a second cavity portion (42) extending between said membrane (30) and the lower opening (21) of the cavity, and wherein said blocking member (51) is insertable into the second cavity portion from the lower open end of the device.

In another embodiment of the present invention, at least a part of the device surrounding the substance receiving portion, the membrane and the blocking member are resistant to alkaline substances, more particularly NaOH.

In another further embodiment of the present invention, the membrane is made of a material, which is at least before use free of absorption properties at least with respect to said substances.

In one embodiment of the present invention, said material is a porous hydrophobic material.

In another further embodiment of the invention, said material is inert to at least said substances.

In another embodiment of the invention, said material has pores of a size in the range of 10 to 40 µm, more particularly, in the range of 20 to 30 µm, and still more particularly, about 25 µm.

In another embodiment of the invention, the device is configured for being mounted on a vacuum manifold when the blocking member (51) is spaced away from the membrane (30) so as to allow application of vacuum to the lower surface of the membrane (31b).

In another embodiment of the invention, said blocking member has an extension along the axis (X), which is at least not less than an extension of the second cavity portion along this axis.

In another embodiment of the invention, the device comprises a plurality of the substance receiving portions constituting an array of wells (40), and a corresponding plurality of blocking members, each configured for taking positions relative to the corresponding substance receiving portion.

In another embodiment of the invention, the device constitutes a part of a system (3) comprising:

an upper plate (10) having an upper surface (15), a lower surface (12) and a plurality of first well portions (41) extending therebetween, each having a top open end at the upper surface and a bottom open end at the lower surface, each first well portion constituting said substance receiving portion (41); and a membrane sheet (30) configured to be assembled with the upper plate (10) at its lower surface (12) so that an area of the membrane closest to the lower open end of each first well portion and corresponding thereto in shape and dimension constitutes a bottom of the first well portion (32).

In another embodiment of the invention, said system further comprises a sealing arrangement (60) for forming a seal around said area of the membrane (32) and the corresponding lower open end of the first well portion.

In another embodiment of the invention, said sealing arrangement (60) is in the form of an upper sealing sheet (60a), optionally made of silicon, having a plurality of upper seal openings (65a) corresponding in shape and dimension to the bottom open end of the first well portions, the upper sealing sheet being configured for mounting between the upper plate (10) and the membrane (30) with its openings in coaxial alignment with the first well portions (41).

In another embodiment of the invention, said system further comprises a lower plate (20) having an upper surface (22), a lower surface (25) and a plurality of second well portions (42) extending therebetween and having cross-sectional shape and dimension corresponding to those of the first well portions, each second well portion having a top open end at the upper surface of the lower plate and a bottom open end at the lower surface of the lower plate; the upper (10) and lower plates (20) being configured for securing to each other with the membrane (30) sandwiched therebetween so that each pair of corresponding first (41) and the second (42) well portions is coaxially aligned to form one well and are separated by said area of the membrane (32).

In another embodiment of the invention, said system further comprises a sealing arrangement forming a seal around said area of the membrane and the top open end of the second well portion.

In another embodiment of the invention, said sealing arrangement is in the form of a lower sealing sheet (60b), optionally made of silicon, having a plurality of lower seal openings (65b) corresponding in shape and dimension to the top open end of the second well portions, the sealing sheet being configured for mounting between the lower plate (20) and the membrane (30) with its openings in coaxial alignment with the second well portions (42).

In another embodiment of the invention, one of the first and second plates comprises locks (70) for securely holding together the upper and lower plates, the membrane and the upper and lower sealing sheets forming thereby an assembly with open-ended wells (100).

In another embodiment of the invention, said system further comprises a blocking base (50) with said blocking members (51) each having a blocking flange (53) corresponding in shape and dimension to said area of the membrane (32).

In another embodiment of the invention, said blocking members are in the form of a plurality of posts protruding from the blocking base's upper surface, said blocking surfaces being constituted by top surfaces of the posts.

In another embodiment of the invention, the system comprises locks (80) for securely holding the blocking base (50) in fixed relation relative to the upper (10) and lower plates (20), when the blocking member (51) is in close proximity to the membrane (30).

In another embodiment of the invention, said assembly (100) is configured for being mounted on a vacuum manifold so that the bottom open ends of the second well portions (21) are exposed for applying vacuum thereto, when said blocking members (51) are spaced away from the membrane.

Another aspect of the invention relates to an in-situ process of sample preparation for detecting the presence and/or quantifying clottable fibrinogen, the process comprising a number of steps and involving at least two substances, one of which comprises fibrinogen and the other one comprises a proteolytic enzyme, which is capable of forming fibrin when it reacts with fibrinogen, said steps being at least the following:
  (a) providing a device according to the invention;
  (b) forming a clot by mixing said at least two substances on the membrane in the substance receiving portion;
  (c) washing the clot with a liquid in the substance receiving portion;
  (d) removing the liquid by applying vacuum at the bottom of the substance receiving portion and/or to the lower opening (21) of the cavity when the blocking member (51) is spaced away from the membrane (30), thereby withdrawing the liquid from the substance receiving portion (41) through the membrane via the lower opening;
  (e) optionally, repeating steps (c) and (d) a number of times;
  (f) bringing the blocking member (51) to the position in close proximity to the membrane; and
  (g) solubilizing the clot in the substance receiving portion with a suitable aqueous solution.

In some embodiments, steps (b) to (g) are carried out in-situ or in the same substance receiving portion.

In one embodiment of the invention, the aqueous solution comprises an alkaline substance and/or a chaotropic agent.

In another embodiment of the invention, the process further includes incubating the mixture obtained in step (b).

In another further embodiment of the invention, said applying vacuum in step (d) is performed by mounting the device on a vacuum manifold so that the bottom open ends of the second well portions (21) are exposed for applying vacuum thereto, when said blocking member (51) is away from the membrane.

In another embodiment of the invention, said number of times in step (e) does not exceed 10.

Yet another object of the invention is to provide a device for performing an in-situ preparation of a sample, said preparation comprising a number of steps and involving at least two substances, the device comprising:
  at least one elongated cavity (40), said cavity having upper and lower openings (11, 21) spaced along a longitudinal axis (X) of the device; said cavity having a substance receiving portion (41) extending between a top open end and a bottom of the substance receiving portion, and having dimensions sufficient to receive therein through the upper opening a predetermined amount of material required for each of said steps; and
  a membrane (30) constituting the bottom of the substance receiving portion and having such a structure as to allow fluid disposed in the substance receiving portion at least in one of the steps, to be transferred therefrom through the membrane towards the lower open end of the cavity (21) only when vacuum is applied thereto via the lower opening;
  wherein the membrane is made of a hydrophobic material, which is free of absorption properties at least with respect to said substances, thereby allowing a clot formed thereon in the substance receiving portion by mixing said substances and, optionally, incubating the mixture in the substance receiving portion, to cover the membrane only partially, more particularly, in the range of 50-80% of the membrane area.

In one embodiment of the invention, said elongated cavity (40) comprises a first cavity portion constituted by said substance receiving portion (41), and a second cavity portion (42) extending between said membrane (30) and the lower opening (21) of the cavity.

In another embodiment of the invention, at least a part of the device surrounding the elongated cavity and the membrane are resistant to alkaline substances, more particularly NaOH.

In another embodiment of the invention, said material is porous.

In another embodiment of the invention, said material is inert to at least said substances.

In another embodiment of the invention, said material has pores of a size in the range of 10 to 40 µm, more particularly, in the range of 20 to 30 µm, and still more particularly, about 25 µm.

In another embodiment of the invention, the device is configured for being mounted on a vacuum manifold so as to allow application of vacuum to the lower surface of the membrane (31b).

In another embodiment of the invention, the device comprises a plurality of the elongated cavity constituting an array of wells.

In another embodiment of the invention, the device constitutes a part of a system (3) comprising:

an upper plate (10) having an upper surface (15), a lower surface (12) and a plurality of first well portions (41) extending therebetween, each having a top open end at the upper surface and a bottom open end at the lower surface, each first well portion constituting said substance receiving portion (41); and a membrane in the form of a sheet (30) configured to be assembled with the upper plate (10) at its lower surface (12) so that an area of the membrane closest to the bottom open end of each first well portion and corresponding thereto in shape and dimension constitutes a bottom of the first well portion (32).

In one embodiment of the invention, said system further comprises a sealing arrangement (60) for forming a seal around said area of the membrane (32) and the corresponding bottom open end of the first well portion.

In one embodiment of the invention, said sealing arrangement (60) is in the form of an upper sealing sheet (60a), optionally made of silicon, having a plurality of upper seal openings (65a) corresponding in shape and dimension to the bottom open end of the first well portions, the upper sealing sheet being configured for mounting between the upper plate (10) and the membrane (30) with its openings in coaxial alignment with the first well portions.

In one embodiment of the invention, said system further comprises a lower plate (20) having an upper surface (22), a lower surface and a plurality of second well portions (42) extending therebetween and having cross-sectional shape and dimension corresponding to those of the first well portions, each second well portion having a top open end at the upper surface of the lower plate and a bottom open end at the lower surface of the lower plate; the upper (10) and lower plates (20) being configured for securing to each other with the membrane (30) sandwiched therebetween so that each pair of corresponding first (41) and the second (42) well portions is coaxially aligned to form one well and are separated by said area of the membrane (32).

In one embodiment of the invention, said system further comprises a sealing arrangement forming a seal around said area of the membrane and the upper open end of the second well portion.

In another embodiment of the invention, said sealing arrangement is in the form of a lower sealing sheet (60b), optionally made of silicon, having a plurality of lower seal openings (65b) corresponding in shape and dimension to the top open end of the second well portions, the sealing sheet being configured for mounting between the lower plate (20) and the membrane (30) with its openings in coaxial alignment with the second well portions (42).

In another embodiment of the invention, one of the first and second plates comprises locks (70) for securely holding together the upper and lower plates, the membrane and the upper and lower sealing sheets forming thereby an assembly with open-ended wells (100).

In another embodiment of the invention, said assembly (100) is configured for being mounted on a vacuum manifold so that the bottom open ends of the second well portions (21) are exposed for applying vacuum thereto.

Another object of the invention is to provide an in-situ process of a sample preparation for detecting the presence and/or quantifying clottable fibrinogen, the process comprising a number of steps and involving at least two substances, one of which comprises fibrinogen and the other one comprises a proteolytic enzyme, which is capable of forming fibrin when it reacts with fibrinogen, said steps being at least the following:

(a) providing a device according to the invention;
(b) forming a clot by mixing said at least two substances on the membrane in the substance receiving portion, wherein, due to the hydrophobic nature of the membrane, the clot covers the membrane only partially, more particularly, in the range of 50-80% of the membrane area;
(c) washing the clot with a liquid in the substance receiving portion;
(d) removing the liquid by applying vacuum at the lower opening of the cavity and thereby withdrawing liquid from the substance receiving portion;
(e) optionally, repeating steps (c) and (d) a number of times;
(f) preventing fluid communication between the substance receiving portion (41) and lower open end (21) through the membrane; and
(g) solubilizing the clot in the substance receiving portion with a suitable aqueous solution.

In some embodiments, steps (b) to (g) are carried out in-situ or in the same substance receiving portion, cavity portion and/or well.

In one embodiment of the invention, the amount of said substances is such that the formed clot has dimensions smaller than the dimensions of the membrane constituting the bottom of the substance receiving portion, so that the clot will not completely cover the surface of the membrane.

In another embodiment of the invention, the aqueous solution comprises an alkaline substance and/or a chaotropic agent.

In another embodiment of the invention, the process further includes incubating the mixture obtained in step (b).

In another embodiment of the invention, said applying vacuum in step (d) is performed by mounting the device on a vacuum manifold so that the bottom open ends of the second well portions (21) are exposed for applying vacuum thereto.

In another embodiment of the invention, said number of times in step (e) does not exceed 10.

In another aspect the invention relates to a kit for assembling a system (1) comprising an array of wells (40), each having the form of an elongated cavity extending between a top well open end (11) and a bottom well open end (21), the kit comprising:

an upper plate (10) having an upper surface (15), a lower surface (12) and a plurality of first well portions extending therebetween, each first well portion having a top open end at the upper surface and a bottom open end at the lower surface; and a lower plate having an upper surface (22), a lower surface (25) and a plurality of second well portions (42) extending therebetween and having cross-sectional shape and dimension corresponding to those of the first well portions (41), each second well portion having a top open end at the upper surface of the lower plate and a bottom open end at the lower surface of the lower plate;

wherein the upper (10) and lower plates (20) are configured for use with a membrane sheet (30) to be sandwiched therebetween when the plates are fixed to each other so that the first and the second well portions (41, 42) are coaxially aligned to form said well (40) and are separated by the membrane (30), the top end of each first well portion constituting the first well open end (11), and the bottom end of each second well portion (21) constituting the second well open end.

In one embodiment of the invention, the kit further comprises said membrane sheet (30).

In another embodiment of the invention, the kit further comprises an upper sealing sheet (60*a*), optionally made of silicon, formed with a plurality of upper seal openings (65*a*) having a shape and dimension corresponding to the cross-sectional shape and dimension of the first well portions (41), wherein when the system is assembled, the upper seal openings are in coaxial alignment with the first well portions, the upper sealing sheet being one of the following:

permanently attached to the lower surface of the upper plate and constituting an integral part thereof;

permanently attached to, and constituting an integral part of, the membrane on its one side; or configured for mounting between the upper plate and the membrane, when assembling the system.

In another embodiment of the invention, the kit further comprises a lower sealing sheet (60*b*), optionally made of silicon, formed with a plurality of lower seal openings (65*b*) having a shape and dimension corresponding to the cross-sectional shape and dimension of the second well portions (42), wherein, when the system is assembled, the lower seal openings are in coaxial alignment with the second well portions, the lower sealing sheet being one of the following:

permanently attached to the upper surface of the lower plate and constituting its integral part;

permanently attached to, and constituting an integral part of, the membrane on its side opposite the side to which the upper sealing sheet is attached; or configured for mounting between the lower plate and the membrane, when assembling the system.

In another embodiment of the invention, one of the first (10) and second (20) plates comprises locks (70) for locking together these plates, the membrane and, optionally, the upper and lower sealing sheets disposed between the membrane and respective upper and lower plates, forming thereby an open-ended assembly (100).

In another embodiment of the invention, the kit further comprises a blocking base (50) having a plurality of blocking flanges (53) each corresponding in shape and dimension to those of said area of the membrane, the blocking base being configured for taking one position, in which each blocking surface is disposed in close proximity to the corresponding area of the membrane and fully covers it if seen from the direction of the well bottom open end so as to prevent the possibility of fluid communication between the first well portion and the second well open end through the membrane, and another position, in which the blocking surface is spaced from the bottom well open end in the direction away from the membrane so as to allow said fluid communication.

In another embodiment of the invention, said blocking base is formed with a plurality of posts (51) protruding from its upper surface, said blocking surfaces being constituted by the top surfaces of the posts.

In another embodiment of the invention, said blocking base comprises locks (80) for locking thereto said open-ended assembly (100), when the blocking base is away from the membrane.

In another embodiment of the invention, said open-ended (100) assembly is configured for being mounted on a vacuum manifold so that the bottom well open ends are exposed for applying vacuum to the wells (40).

In another embodiment of the invention, said membrane is made of a hydrophobic material.

In another embodiment of the invention, said membrane is made of a material, which is free of absorption properties.

Still another aspect of the invention is to provide a method for quantifying clottable fibrinogen in a fibrinogen containing sample, the method comprising steps (a) to (g) as disclosed above, and further comprising:

(h) transferring a predetermined portion of the solubilized clot of step (g) to a cuvette;

(i) measuring the protein absorbance of the portion using a spectrophotometer; and (j) determining the clottable fibrinogen present in the sample a fibrinogen standard containing a known amount of clottable fibrinogen.

In one embodiment of the invention, the step of measuring protein absorbance is carried out by measuring Optical Density at a wavelength of 280 nm and at a wavelength of 320 nm, and reducting the obtained Optical Density at 320 nm from the obtained Optical Density at 280 nm.

In another embodiment of the invention, the fibrinogen standard is subjected to steps (a) to (i) as the fibrinogen containing sample. Yet in another aspect the invention relates to a system for performing an in-situ preparation of a sample, the system comprising:

an upper plate (10) having an upper surface (15), a lower surface (12) and an array of first well portions (41) extending therebetween;

a lower plate (20) having an upper surface (22), a lower surface (25) and an array of second well portions (42) extending therebetween and corresponding to the array of the first well portions (41);

an upper sealing sheet (60*a*) having an array of respective upper seal openings (65*a*) and a lower sealing sheet (60*b*) having an array of respective lower seal openings (65*b*), each corresponding to the arrays of the first and second well portions (41, 42) in the upper and lower plates (10, 20);

a membrane sheet (30) having an upper surface (31*a*) and a lower surface (31*b*) and having such a structure as to allow fluid disposed at its upper surface (31*a*) to be transferred through the membrane (30) towards its lower surface (31*b*) only when vacuum is applied to the lower surface (31*b*);

locks (70) in the lower plate (20) configured for securely holding together the upper and lower plates (10, 20), the membrane (30), the upper sealing sheet (65*a*) between the upper plate and the membrane, and the lower sealing sheet (65*b*) between the membrane and the lower plate, with all the arrays being aligned so as to form an assembly (100) with an array of wells (40) each having a top open end (11) at the upper surface of the upper plate, a bottom open end (21) at the lower surface of the lower plate, the first well portion (41) extending between the top open end and the upper surface of the membrane (31*a*), and the second well portion (42) extending between the lower surface of the membrane and the bottom open end, with the upper and lower surfaces of the membrane being sealed around the first and second well portions against fluid when transferred through the membrane from the first well portion into the second well portion;

the system further comprising:

a blocking base (50) with an array of posts (51) protruding from its upper surface and configured to be received in the second well portions (42) when inserted therein from the bottom open end, to prevent fluid disposed at the membrane upper surface to be transferred through the membrane into the second well portion;

the blocking base (50) having a plurality of locks (80) for securely holding the blocking base (50) in fixed relation relative to the assembly (100), when the blocking posts (51) are received in the second well portions (42).

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
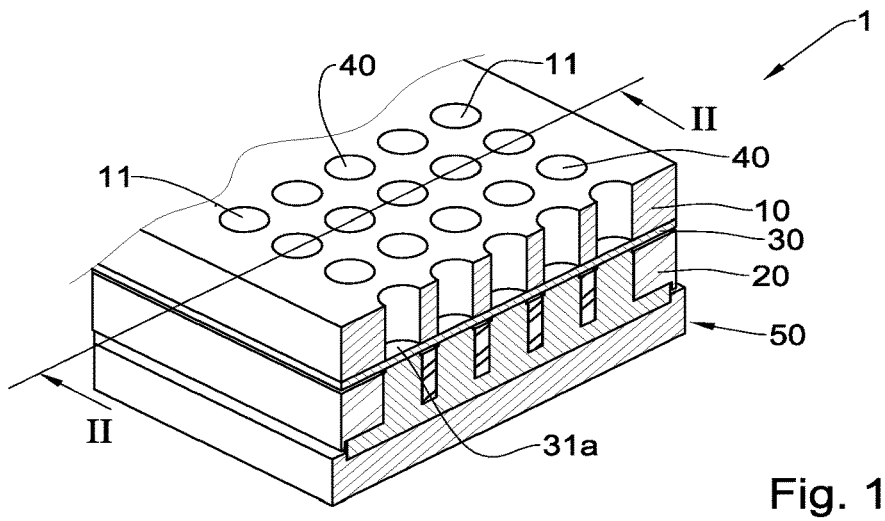
FIG. 1 is a schematic perspective view of a system according to one embodiment of the presently disclosed subject matter.
Figure 2A:
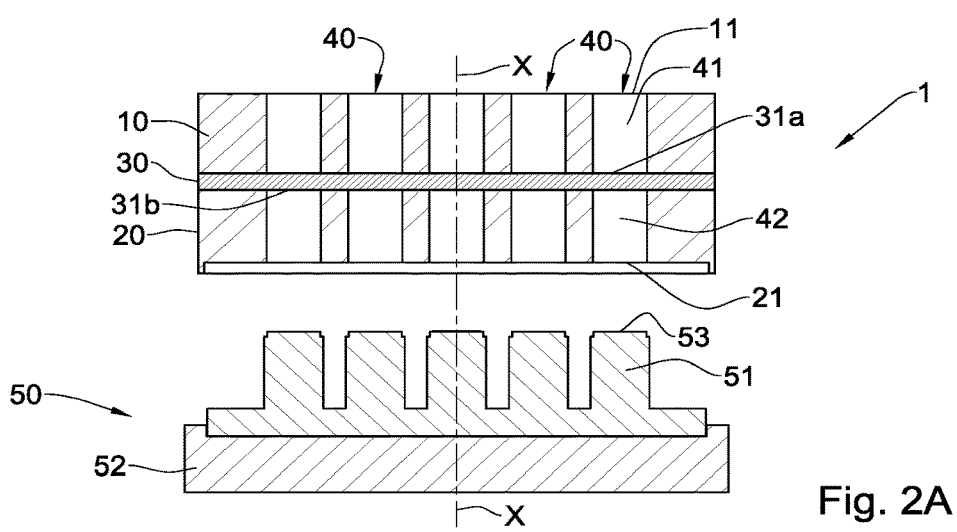
FIGS. 2A and 2B are schematic cross-sectional views of the system of FIG. 1 taken along a plane II-II, with its blocking base being in a first and a second position, respectively.
Figure 2B:
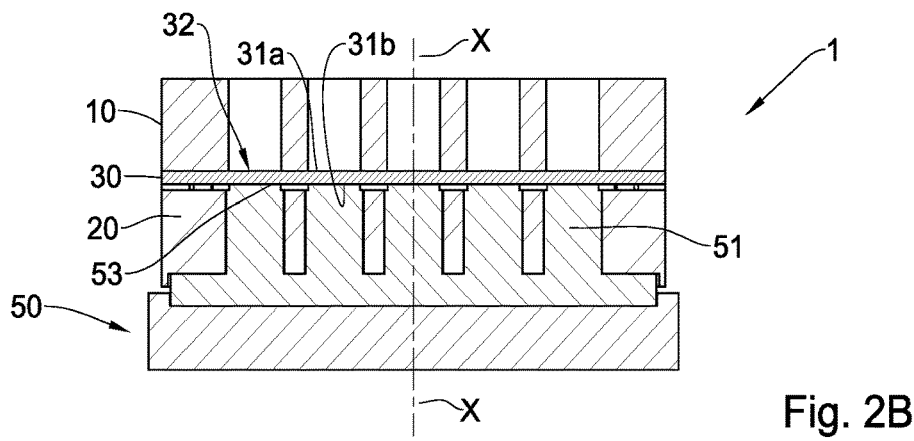

FIGS. 1, 2A and 2B are schematic perspective and cross-sectional views of a system 1, according to one embodiment of the presently disclosed subject matter, for in-situ preparation of a plurality of fibrinogen containing samples (hereinafter: 'test samples') e.g. by a procedure including steps (a) to (c) described in the Background part of the present specification, for detecting the presence of and/or quantifying, fibrinogen using a solution containing a proteolytic enzyme, which is capable of forming fibrin when it reacts with fibrinogen e.g. thrombin.

The system 1 comprises an upper plate 10 with an array of first cavity portions 41 with upper openings 11, a lower plate 20 with a corresponding array of second cavity portions 42 with lower openings 21, and a porous membrane therebetween 30, assembled so that the first cavity portions of the upper plate are coaxially aligned with second cavity portions of the lower plate with respect to a longitudinal axis X, and the membrane 30 separates between them, forming thereby an array of elongated cavities 40, each configured for the preparation of a single test sample. The system 1 further comprises a blocking plate 50 having a plurality of posts 51 upwardly protruding therefrom, each configured for being received in a corresponding lower opening 21.

As seen in FIG. 1 and FIG. 2A, each elongated cavity 40 constitutes a well with its top and bottom open ends constituted by the upper and lower openings 11 and 21 of the plates 10 and 20, respectively, which is divided by the membrane 30 into a first well portion constituted by the first cavity portion 41 and functioning as a substance receiving portion, and a second well portion constituted by the second cavity portion 42 and configured to serve as a passage via which the post 51, when inserted therein from the second open end 21 of the cavity, can block access to the membrane from the bottom open end, as shown in FIG. 2B.

The membrane 30 is in the form of a sheet made of a porous material free from absorption properties with respect to protein, such as to fluid disposed thereon in the substance receiving portion 41, to pass through the membrane when vacuum is applied thereto via the bottom open end/lower opening 21. The membrane material is a hydrophobic material inert to the substances mentioned above. The membrane has pores of a size in the range of 10 to 40 µm, more particularly, in the range of 20 to 30 µm, and still more particularly, about 25 µm.

Each substance receiving portion 41 has dimensions sufficient to receive therein through the top open end/upper opening 11 a predetermined amount of substances required for each step of the process.

Each post 51 has an axial extension, which is at least not less than the axial extension of the second cavity portion 42 and has a flange 53 having a shape and dimensions corresponding to those of the second portion of the well at least at its location close to the membrane 30.

The blocking base 50 is configured for moving the posts 51 from a first position, in which the flanges 53 of the posts 51 are spaced from the bottom open ends 21 in the direction away from the membrane 30 so as to allow fluid communication between the first well portion 41 and the second well portion 42 through the membrane 30, and a second position in which each flange 53 is disposed in close proximity to or contact with the corresponding area 32 of the lower surface 31b of the membrane 30 within each well and fully covers it if seen from the direction of the well bottom open end 21 so as to prevent the possibility of the above fluid communication.

The upper plate 10 including the walls of the first well portions 41, the lower plate 20 including the walls of the second well portions 42, and the blocking base 50 including the posts 51, are made of materials resistant to alkaline substances, e.g. NaOH. One example of such material is stainless steel, and more particularly ST-303. Each of the listed elements can be made of more than one material. For example, the blocking posts 51 can be made of a material or have a coating, having higher hydrophobic properties and lower coefficient of friction than those of a material of which the blocking plate 52 is made. In particular, the blocking plate 52 can be made from stainless steel, such as ST-303, and the blocking posts 51 can be made from Teflon.

The blocking plate 52 and the posts 51 can all be produced as a unitary body as in the described example. Alternatively, these elements can be produced separately and assembled to form the blocking base 50. The plate can be constructed so as to be stationary or move only horizontally with respect to the reminder of the system, being permanently spaced from the lower plate 20, and can have a mechanism for moving the posts 51 axially between their above described two positions (not shown).

The system 1 is configured for being mounted on a vacuum manifold (not shown), so that the bottom open ends 21 are exposed for applying therethrough vacuum to the wells.

The system 1 can further comprise a sealing arrangement (not shown in FIGS. 2A and 2B), for sealing the area of the wells between the membrane 30 and at least one of the upper plate 10 or the lower plates 20.

With the above structure of the system, it constitutes a multi-well array, in which each well functions as a single testing tube with a dedicated blocking post 51, movable between its first position outside the tube and second position inside the tube.

The above system can be used for in-situ process of preparation of test samples from a fibrinogen containing sample, using a solution containing proteolytic enzyme, which is capable of forming fibrin when it reacts with fibrinogen e.g. thrombin, as follows:

(a) disposing in the substance receiving portion 41 of each well a predetermined amount of a thrombin containing solution and a predetermined amount of a fibrinogen containing sample, to obtain their mixture, on the membrane 30, and optionally placing the system in an incubator (not shown) to facilitate the formation of the mixture in the form of a fibrin clot, wherein the blocking post 51 associated with each well is in its first position (FIG. 2A) i.e. outside the tube;

(b) mounting the system 1 on a vacuum manifold (not shown), wherein the bottom open ends 21 face the vacuum manifold;

(c) washing the clot with a predetermined amount of liquid, such as saline, in the substance receiving portion 41;

(d) removing the liquid together with the "non-clottable" proteins by operating the vacuum manifold to apply vacuum to the membrane 30 at the bottom open ends 21, thereby withdrawing "non-clottable" proteins from the substance receiving portion 41 through the membrane 30 via the bottom open end 21;

(e) optionally, repeating steps (c) and (d) a number of times;

(f) removing the system 1 from the vacuum manifold;

(g) moving the blocking base 50 to bring the posts 51 in their second position (FIG. 2B) i.e. inside the tube; and (h) disposing a predetermined amount of solubilizing solution such as alkali solution comprising alkaline substance and/or chaotropic agent, in the substance receiving portion 41 of each well to facilitate the solubilizing of the clot, producing thereby the test sample.

In some embodiments, steps (a) to (h) are carried out in-situ or in the same substance receiving portion, cavity portion and/or well.

In the above described process, the amount of the substances used in each well is such that the fibrin clot produced in step (a) above has such dimensions that its area of contact with the membrane 30 constituting at the bottom of the substance receiving portion 41, is smaller than the area of the membrane surface so that the clot occupies only a part of the latter area, i.e. does not completely cover the surface of the membrane, which is possible due to the hydrophobic nature of the membrane.

Figure 3:
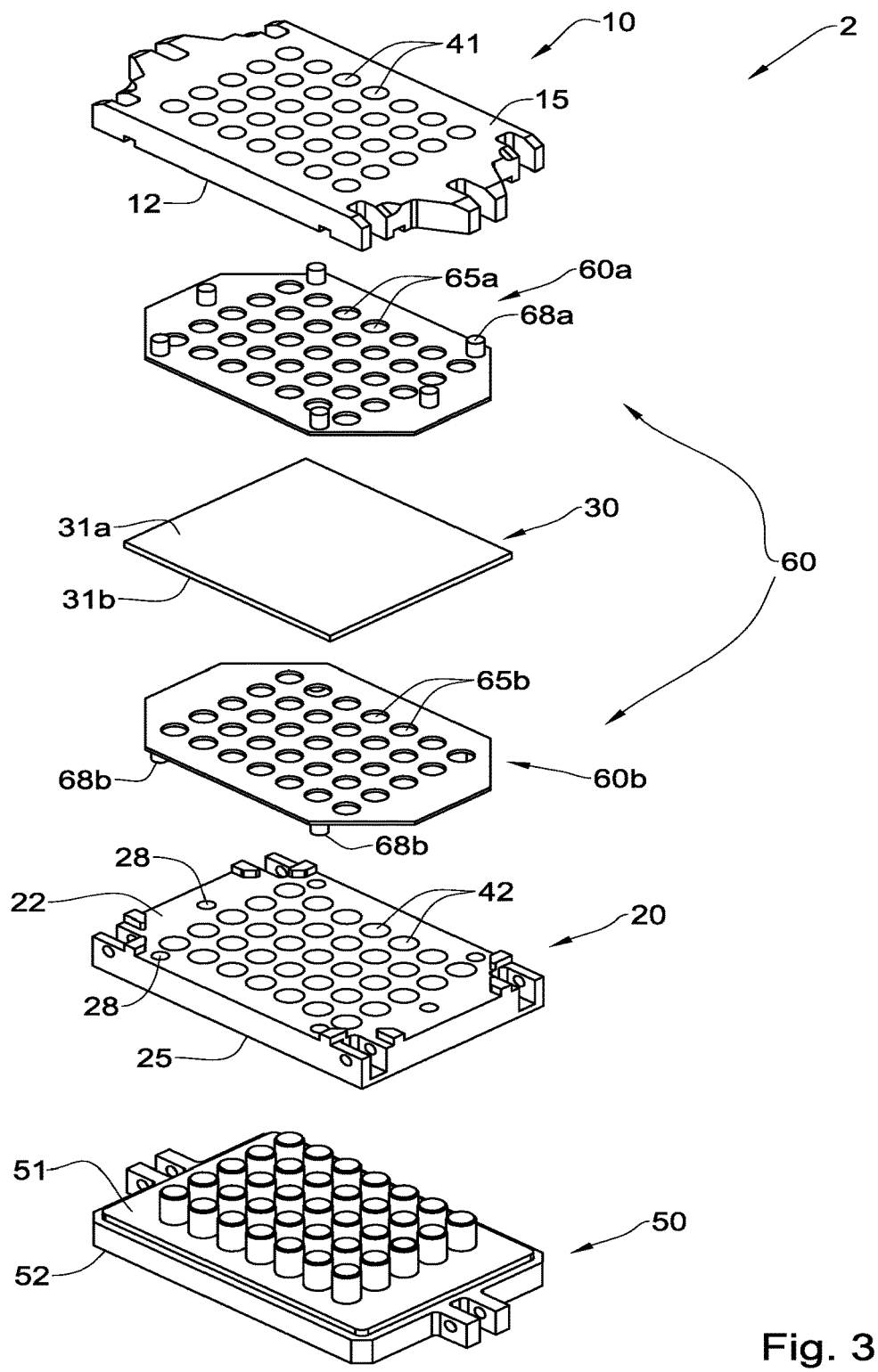
FIG. 3 is an exploded view of a system according to another embodiment of the presently disclosed subject matter.

FIG. 3 illustrates a system 2 according to another embodiment of the presently disclosed subject matter, which is similar to the system 1 as far as the structures of its upper plate 10, lower plate 20, membrane 30 and blocking base 50 are concerned, but further includes a sealing arrangement 60. In FIG. 3, a lower surface of the upper plate 10 is designated as 12, the upper surface of the lower plate 20 is designated as 22 and the sealing arrangement are in the form of upper and lower sealing members designated as 60a and 60b, respectively.

Each of these sealing members 60a, 60b has a form of a sheet of a shape and dimensions corresponding to the respective lower surface of the upper plate 12 or upper surface of the lower plate 22, and is mounted, accordingly, either between the lower surface of the upper plate 12 and the membrane 30 at its side facing that surface, or between the upper surface of the lower plate 22 and the membrane 30 at its side facing that surface.

The upper sealing member 60a has a plurality of upper seal openings 65a having a shape and dimension corresponding to the cross-sectional shape and dimension of the first well portions 41. Thus, when the upper sealing member 60a is sandwiched between the upper plate 10 and the membrane 30 with its openings 65a coaxially aligned with the first well portions 41, a seal is formed around the first well portions e.g. preventing fluid passing from the first well portions towards the membrane from reaching areas of the membrane other than the area 31.

The lower sealing member 60b has a plurality of lower seal openings 65b having a shape and dimension corresponding to the cross-sectional shape and dimension of the second well portions 42. Thus, when the lower sealing member 60b is sandwiched between the lower plate 20 and the membrane 30 with its openings 65b coaxially aligned with the second well portions 42, a seal is formed around the second well portions e.g. preventing fluid passing from through the area 32 of the membrane towards the second well portions 42, from reaching areas of the membrane other than the area 32.

Both upper and lower sealing members can be made of material such as silicon, allowing their cleaning/washing.

In general, the upper and the lower sealing members 60a and 60b can be either permanently or detachably attached to the respective upper and lower plates 10 and 20, and they all can have respective positioning male and female portions whose engagement ensures required mutual disposition of the sealing members and the upper and lower plates. In particular, in the embodiment shown in FIG. 3, the upper and lower sealing members 60a and 60b have a plurality of pins 68a and 68b disposed along their opposite edges and configured for being tightly received in corresponding bores 18 (not seen) and 28 in the upper and lower plates 12 and 22, correspondingly.

The system 2 can include a first securing arrangement configured for securing together the upper and lower plates, 10 and 20, with the upper and lower sealing members, 60a and 60b and the membrane 30 therebetween, forming thereby an open-ended assembly (not including the blocking plate 50, which in this case is in its first position), and a second securing arrangement configured for securing to the open-ended assembly, the blocking plate 50 when in the second position, at opposite locations thereof disposed between its areas corresponding to the corners of the upper and lower plates.

More particularly, the upper and lower plates can have a number of corners participating in securing, in which case the first arrangement can be configured for applying equal force to the upper and lower plates at these corners, when the plates are secured together.

Figure 4A:
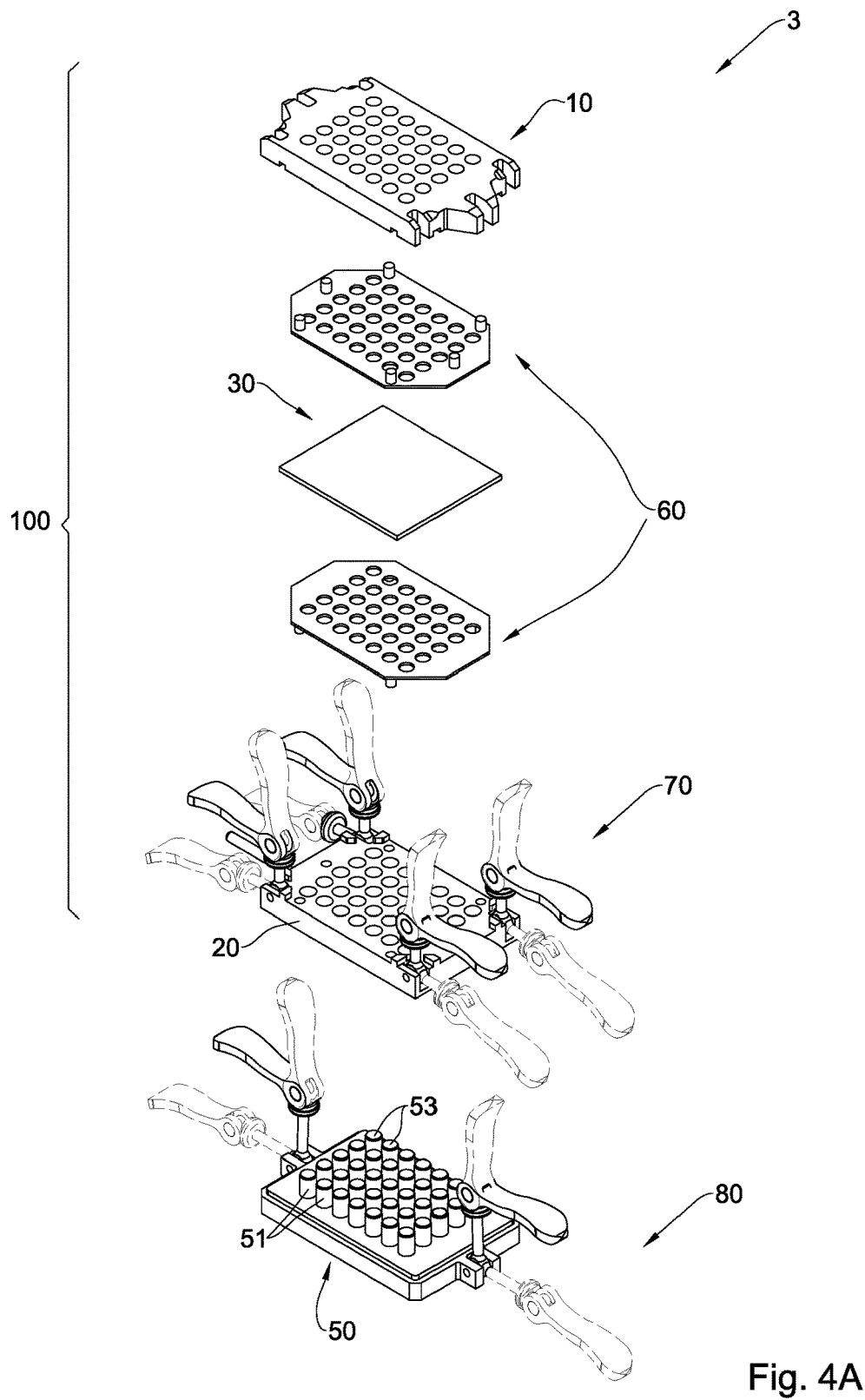
FIG. 4A is an exploded view of a system according to a further embodiment of the presently disclosed subject matter.
Figure 4B:
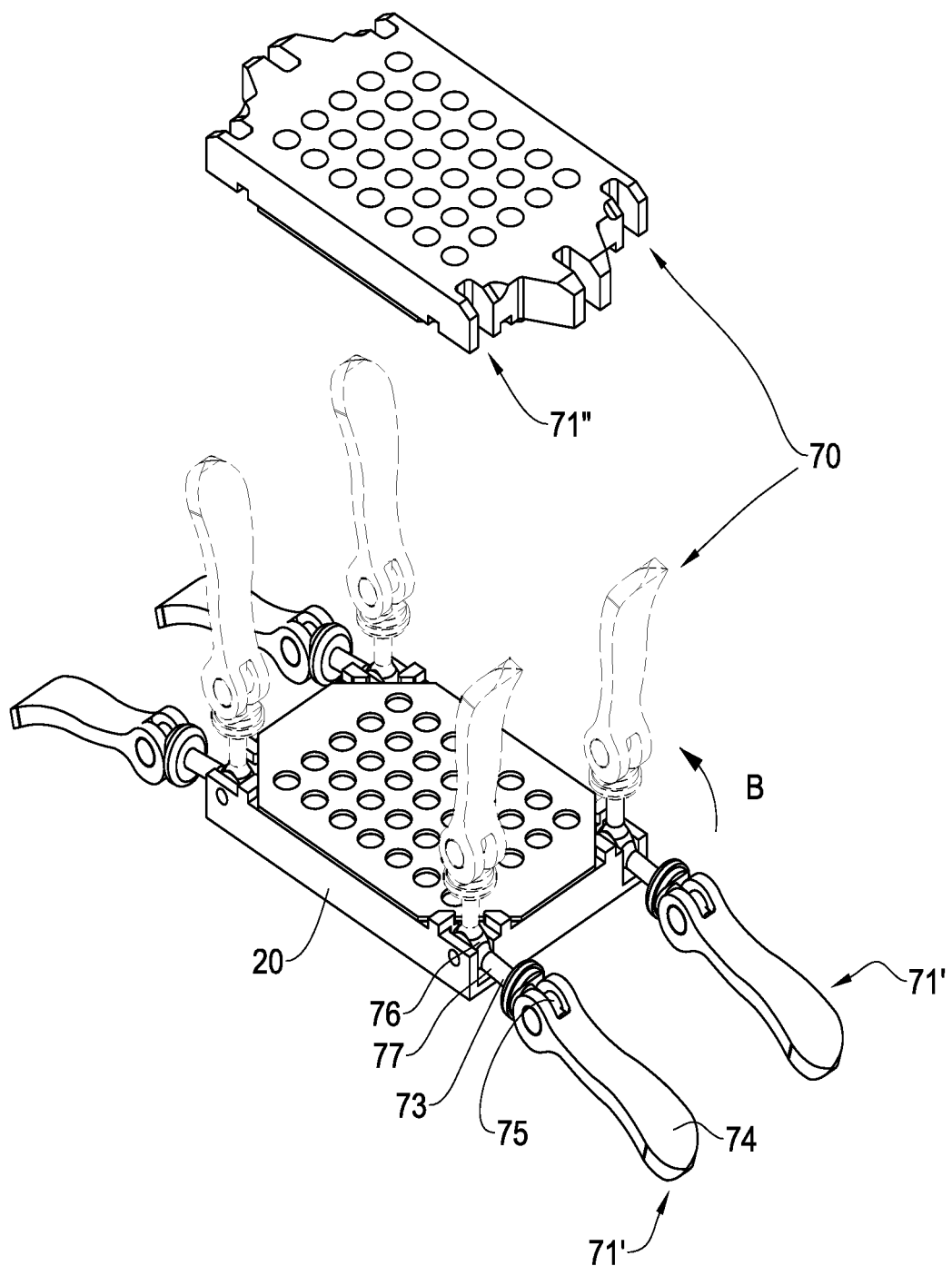
FIG. 4B to 4D are perspective views of the system shown in FIG. 4A, without its blocking plate, at different stages of its assembling.
Figure 4C:
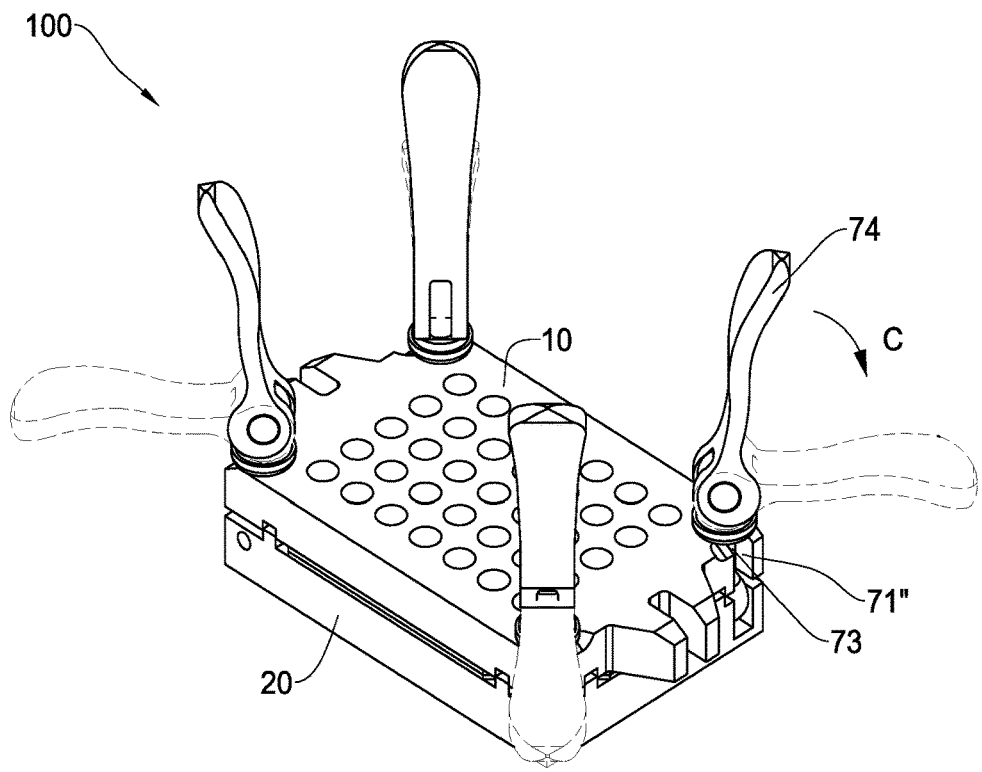
Figure 4D:
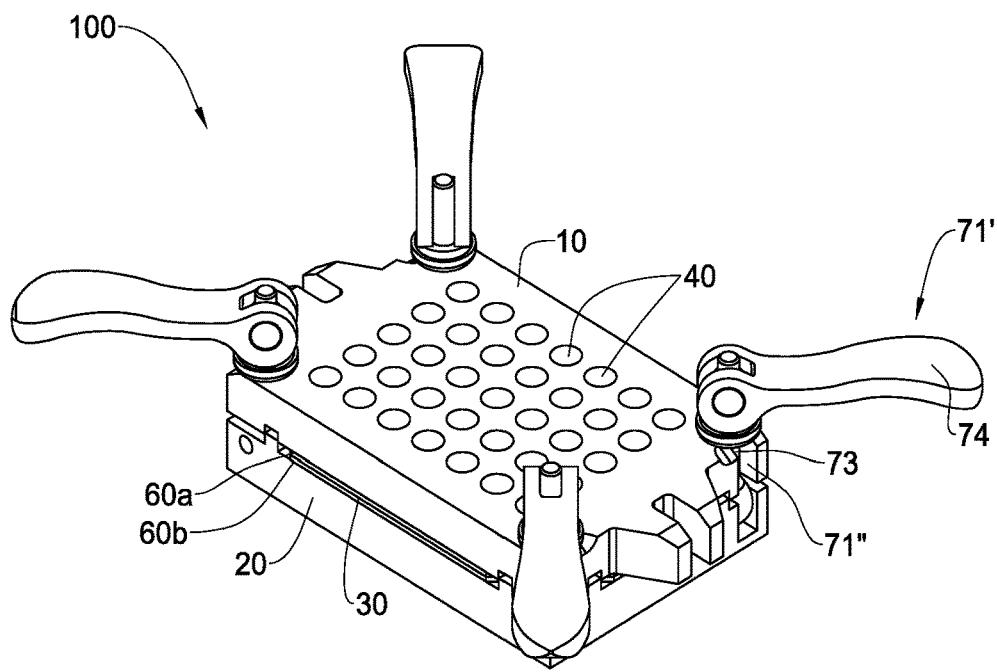
Figure 4E:
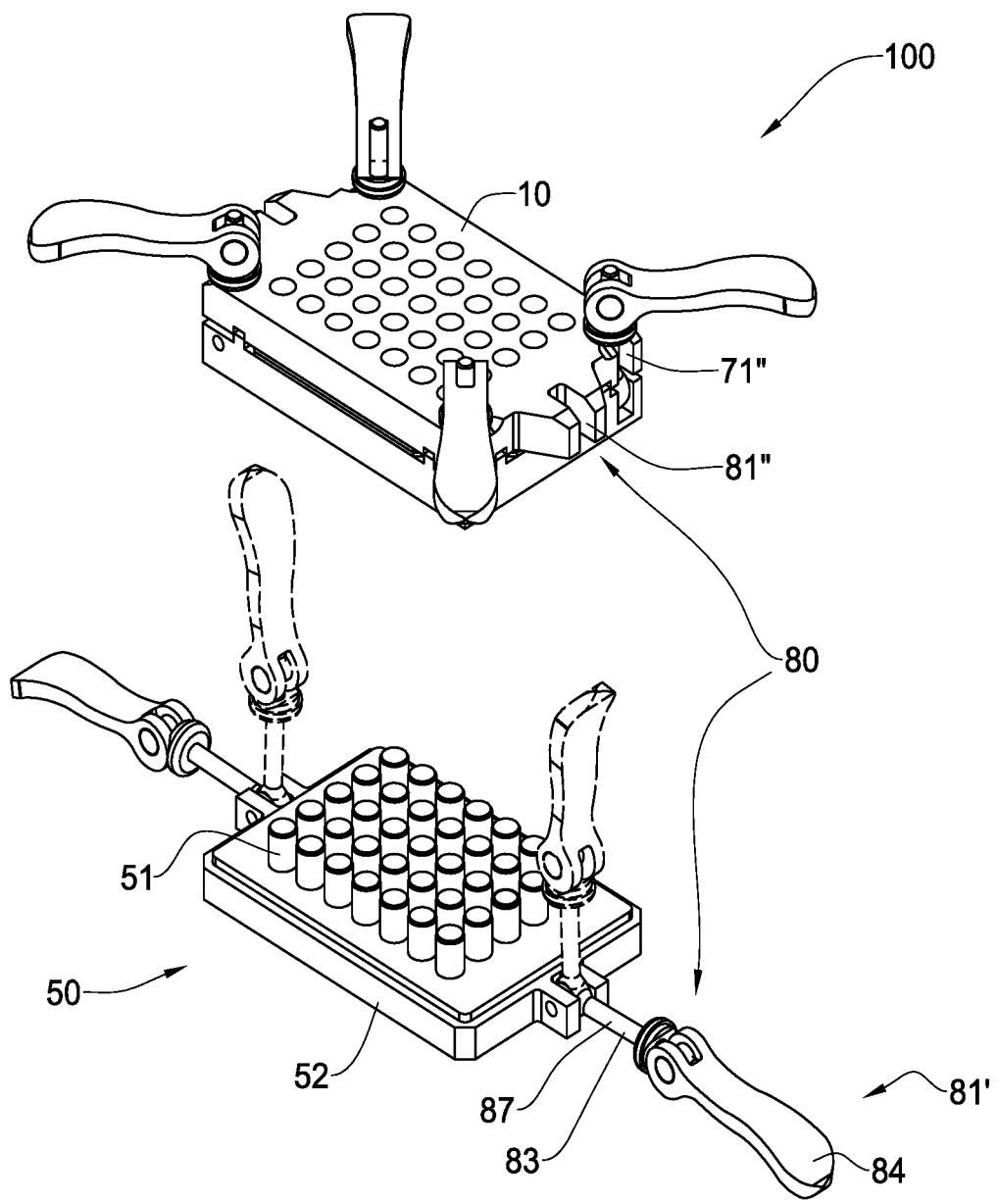
FIGS. 4E to 4G are perspective views of the system shown in FIG. 4A, at different stages of securing its blocking plate to the assembly shown in FIG. 4D.
Figure 4F:
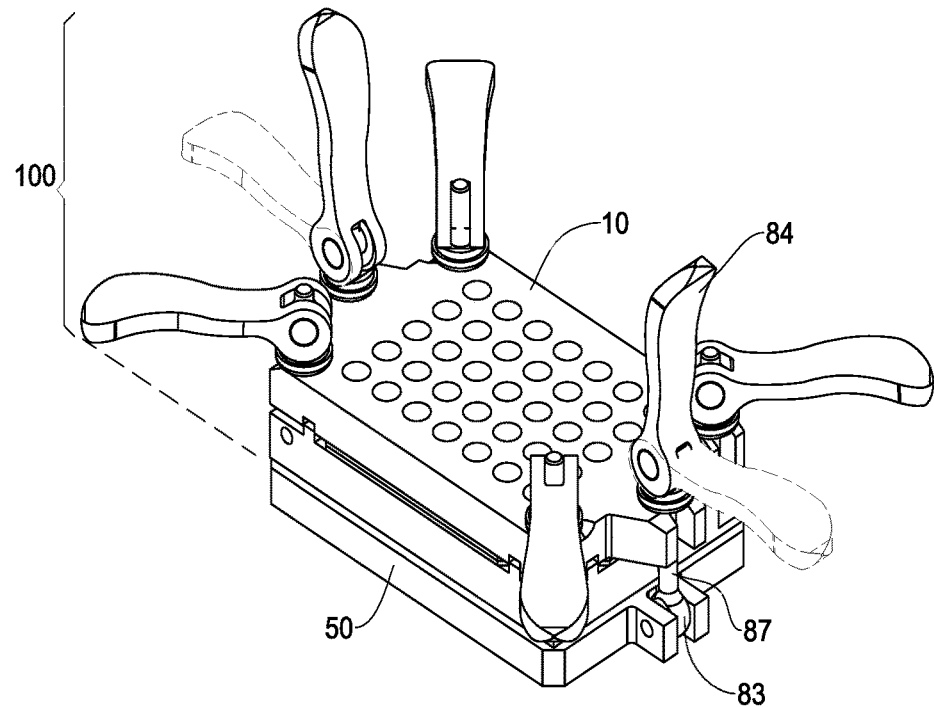
Figure 4G:
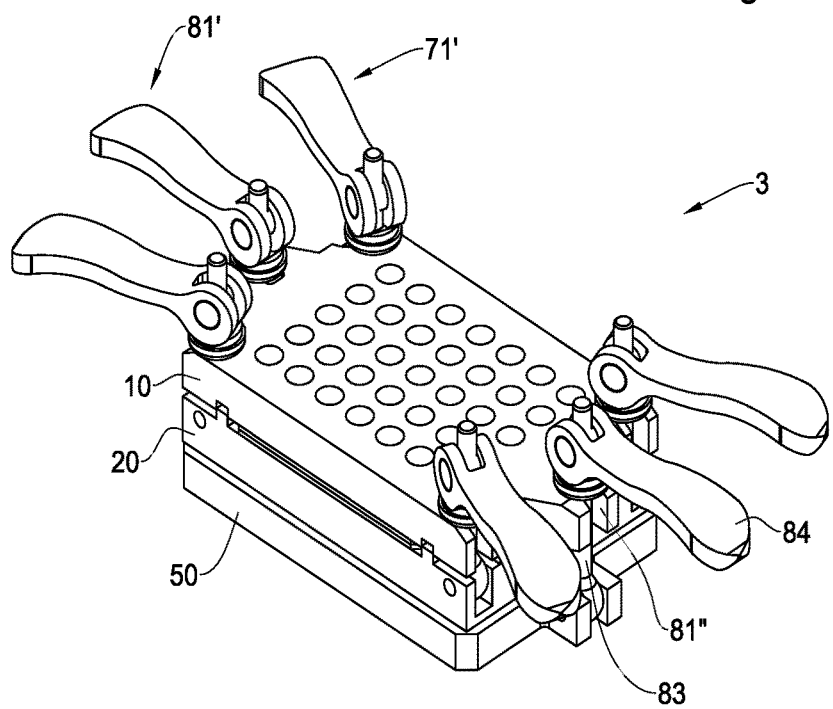

FIG. 4A illustrates a system 3 according to a further embodiment of the presently disclosed subject matter, which is similar to the system 2 as far as the structures of its upper plate 10, lower plate 20, membrane 30, blocking base 50 and sealing arrangement 60 are concerned, but it further includes a first securing arrangement, which in this case are in the form of four identical locking mechanisms 70 shown in more detail in FIGS. 4B to 4D, and a second securing arrangement, which in this case is in the form of two locking mechanisms 80 shown in more detail in FIGS. 4E to 4G.

With reference to FIGS. 4B to 4D, each locking mechanism 70 of the first securing arrangement, comprises a lock 71' attached to the lower plate 20 at least at one of its corners and a lock engaging portion 71" formed at a corresponding corner of the upper plate 10. The lock 71' comprises:

- an alignment member 73 in the form of an eye bolt having and upper end 75, a lower end 76 and an elongated bolt body 77 therebetween, wherein the lower end 76 is hingedly attached to the lower plate 20 with a possibility of the eye bolt to be turned in a direction of an arrow B between a first, horizontal position (with respect to the plate) shown in solid lines, and a second, vertical position (with respect to the plate) shown in dotted lines, as shown in FIG. 4B; and
- a clamping member 74 in the form of an eccentric cam lever mounted to the upper end 75 of the eye bolt 73 with a possibility of being turned in the direction of an arrow C between a first position, in which it is aligned with the alignment member and a second position, in which it is oriented transversely with respect to the alignment member, as shown in FIG. 4C.

The lock engaging portion 71" of the upper plate 10 is in the form of a recess configured to receive therein the bolt body.

In operation, the upper and lower plates 10 and 20, with the membrane 30 and sealing members 60a and 60b therebetween are first aligned prior to their securing to each other; then, the eye-bolt 73 is turned from its horizontal to its vertical position so that the bolt body 77 is received within the lock engaging portion 71" and the eccentric cam lever 74 in its aligned position is disposed above the upper plate, as shown in FIG. 4C; and finally, the eccentric cam lever 74 is turned into its transverse position as shown in FIG. 4D, thereby applying pressure on the upper plate 10. Once this happens in all four locking mechanisms 70, the upper and lower plates are securely clamped to each other, forming an assembly 100 (FIG. 4A, 4D).

With reference to FIGS. 4E to 4G, the locking mechanisms 80 of the second securing arrangement have the same structure and operate in the same manner as the locking mechanism 70, with the main difference being in their location. In particular, locks 81' of the locking mechanisms 80 are attached to the blocking plate 50 in the middle of its opposite edges and a lock engaging portion 81" formed at a corresponding location of the upper plate 10 between the lock engaging portions 71", as shown in FIG. 4E. In some embodiments the "lock engaging portion" is a protrusion in the upper plate.

In operation, the assembly 100 and the blocking member 50 are first aligned prior to their securing to each other; then, the eye-bolt 83 is turned from its horizontal to its vertical position so that the bolt body 87 is received within the lock engaging portion 81" and the eccentric cam lever 84 in its aligned position is disposed above the upper plate, as shown in FIG. 4F; and finally, the eccentric cam lever 84 is turned into its transverse position as shown in FIG. 4G, thereby applying pressure on the upper plate 10. Once this happens in both locking mechanisms 80, the assembly 100 and the blocking plate are securely clamped to each other, forming the system 3 (FIG. 4G).

As clear from the above description the length of the elongated bolt body 77 of the locking mechanism 71 should correspond the total thickness of the upper plate 10, the membrane and sealing members therebeweeen, and the length of the elongated bolt body 87 of the locking mechanism 81 should correspond to the total thickness of the assembly 100.

Any of the systems 1 to 3 described above can be assembled at their manufacturing site or alternatively can be produced as a kit, in which all or at least a part of the components of the systems are to be assembled at the user's site.

Experiments have been performed for comparing results of quantifying clottable fibrinogen concentration in a fibrinogen containing solution obtained using the device and in-situ process according to the presently described subject matter is described below, with those obtained using a fibrinogen containing solution either prepared by a known method of preparation (experiment 1) or having a known value (experiment 2).

Experiment 1

The purpose of this Experiment was to examine the ability of the device and in-situ process according to the presently disclosed subject matter to measure the fibrinogen content in a fibrinogen containing sample (samples 1 and 2, see below). For this purpose, the obtained clottable fibrinogen concentration in the tested samples were compared to the results obtained using the known, validated gravimetric method.

To calculate the clottable fibrinogen concentration in samples 1 and 2 in the assay, the samples were tested in the device side by side with a fibrinogen standard sample (having a clottable fibrinogen concentration of 64 mg/ml).

Tested Samples (Fibrinogen Containing Solutions)

Sample 1 contained 29.8 mg/ml clottable fibrinogen;

Sample 2 contained 70.1 mg/ml clottable fibrinogen.

Known Assessment Method (Known, Validated Gravimetric Method)

The known method for assessing the clottable fibrinogen concentrations in the two samples was a validated gravimetric approach according to the European Pharmacopeia 7.0 (also see: Gaffney P. J. and Wong M. Y. Collaborative study of a proposed International Standard for plasma Fibrinogen measurement. Thrombosis and Heamostasis, 68 (4), pp. 428-432, 1992).

Tested Technique and Method

Below is the description of a device according to the presently disclosed subject matter, used in the experiments.

The device had a rectangular upper plate and a rectangular lower plate made of Stainless Steel (st-303), each plate having 35 open wells. Each plate has a height of 1.5 cm, a length of 12.6 cm, and width 8.5 cm. Each well had a depth of 1.5 cm, a diameter of 0.9 cm, and an area of 0.64 cm$^2$. The device comprised two silicon sealing members, each having a thickness of 0.2 cm, corresponding in length and in width to the two plates, and having holes, which correspond in shape and size to the wells in the plates. A hydrophobic membrane sheet made of polypropylene was used, having a pore size of 25 μm (Merck, cat# PP2514250). The device further comprised four cam lever locks made of Stainless Steel (st-303), located on each corner of the lower plate for holding together the upper and lower plates, the membrane sheet and the two sealing members, forming an assembly with open-ended wells to be used during the in-situ process.

The above elements were assembled according to the following order from bottom to top: the lower plate, a first silicon sealing member, the membrane, the second silicon sealing member, the upper plate, after which these elements were secured to each other by the cam lever locks (hereinafter: 'Assembly I').

The device further comprised a rectangular blocking base made of Stainless Steel (st-303) having 35 blocking posts, the base having a length of 13 cm and a width of 9 cm, and each post having a height of 2.9 cm with an upper surface having a diameter of about 0.8 cm and corresponds in shape to the well opening. The blocking base had two cam lever locks made of Stainless Steel (st-303) and located in the middle of the short sides of the base. The locks were configured for holding together the Assembly I with the blocking base, thereby locating the posts in close proximity to the membrane. The Assembly I was mounted on the blocking base in such a manner that the blocking posts prevented the possibility of fluid leakage through the membrane.

Vacuum manifold (Merck Millipore, cat# MAVM0960R) was used to apply vacuum to the device. It has a height of 5.5 cm, a length of 14.5 cm, a width of 10 cm.

The testing was carried out according to the following steps:

1—A clot was formed within the wells of Assembly I by mixing 50 μl Solution A and 60 μl of Solution B on the membrane sheet (see composition of Solution A and Solution B in Table 1 below).

TABLE 1

Preparation of Solution A and Solution B.

| Solution A* | Solution B |
|---|---|
| 200 μl Saline and 50 μl Sample 1 or 450 μl Saline and 50 μl Sample 2 | 1912 μl Saline 400 μl 0.1M EDTA 88 μl thrombin standard sample (159 IU/ml) |

*The Samples were diluted with saline to be within the acceptable O.D. based on the fibrinogen standard sample. The fibrinogen standard was diluted as sample 2, 450 μl Saline and 50 μl fibrinogen standard.

2—To allow clot formation, the mixture was incubated at room temperature (about 20-25° C.) for 20 minutes. The clot covered about 0.35-0.49 cm$^2$ of the membrane surface (about 55-77% of the well area).

3—Following the clot formation, Assembly I was mounted on the vacuum manifold, and the clots were washed 6 times to remove non-clottable proteins. Each time 900 μl saline were added to each well, and then vacuum was applied to the device at a pressure difference (ΔP) of about 900 mbar, resulting in passage of the washing solution through the membrane.

4—Assembly I was removed from the vacuum manifold and mounted on the blocking base, and secured by the two cam lever locks, placing the posts in close proximity to the membrane, and preventing the possibility of fluid leakage through the membrane.

5—1 ml clot solubilizing solution [7 M urea, 0.2 M NaOH in Phosphate-buffered saline (PBS)] was added to each well.

6—After a 1-hour incubation period at room temperature. In this Experiment, Steps 1-6 are carried out in-situ (in the same well).

7—After the incubation, 100 μl was collected from each well and transferred into an Eppendorf tube and diluted 1:10 with 900 μl H$_2$O.

8—The sample was transferred to a cuvette for quantification of clottable fibrinogen concentration. The measurement of Optical Density (O.D.) was carried out by a spectrophotometer at 280 nm and 320 nm. To measure the final O.D. for clottable fibrinogen calculation, O.D. measurements at 320 nm were subtracted from O.D. measurements at 280 nm, and the exact clottable fibrinogen concentration was calculated based on the subtracted O.D. and the O.D. known fibrinogen standard sample that was subjected to the above steps. Dilutions of the samples were taken into consideration in the calculations.

The results of the examples test are shown in Table 2 below.

TABLE 2

Clottable fibrinogen concentration in Samples 1 and 2.

| Replicate | Clottable fibrinogen (mg/ml) - Sample 1 | Clottable fibrinogen (mg/ml) - Sample 2 |
|---|---|---|
| 1 | 29.9 | 68.7 |
| 2 | 30.6 | 73.2 |
| 3 | 29.9 | 67.2 |
| 4 | 29.1 | 71.7 |
| 5 | 30.6 | 70.2 |
| 6 | 30.6 | 67.2 |
| 7 | 32.1 | 65.7 |
| 8 | 30.6 | 71.7 |
| 9 | 27.6 | 71.7 |
| 10 | 29.1 | 71.7 |
| 11 | — | 68.7 |
| Mean ± SD | 30.0 ± 1.2 | 69.8 ± 2.4 |
| Relative Standard Deviation (RSD, %) | 4.0 | 3.5 |
| Results obtained using the known gravimetric method | 29.8 | 70.1 |

It can be seen that the average results obtained for Samples 1 and 2 using the device and in-situ process according to the presently disclosed subject matter were essentially the same as the results obtained by the time consuming alternative validated method (in which all the steps for the sample preparation were not carried out in the same well).

These results demonstrate the high accuracy of the in-situ process and the suitability of the in-situ process and device of the presently disclosed subject matter to be used for quantifying clottable fibrinogen concentration in a fibrinogen containing solution.

The RSD between the different replicates (3.5-4%) demonstrates the good precision of the test.

Experiment 2

The precision of the in-situ process according to the presently disclosed subject matter to measure the clottable fibrinogen concentration in a sample was corroborated by testing the clottable fibrinogen concentration of an International Standard for a Fibrinogen Concentrate having a known certified value of 10.9 mg/ml (purchased from NIBSC, code 02/242) (hereinafter: 'Sample 3').

Tested Technique and Method

The test was performed using device and in-situ process identical to those described in Experiment 1 above. Clot preparation was carried out as for Sample 1 (see Table 1).

The clottable fibrinogen concentrations obtained using the device and in-situ process described above are shown in Table 3 below.

TABLE 3

Clottable fibrinogen results of an International Standard for fibrinogen concentrate.

| Replicate | Clottable fibrinogen (mg/ml) using the device and method according to the subject matter | Known certified value (mg/ml) - Sample 3 |
|---|---|---|
| 1 | 11.1 | 10.9 |
| 2 | 10.8 | |

TABLE 3-continued

Clottable fibrinogen results of an International Standard for fibrinogen concentrate.

| Replicate | Clottable fibrinogen (mg/ml) using the device and method according to the subject matter | Known certified value (mg/ml) - Sample 3 |
|---|---|---|
| 3 | 10.4 | |
| 4 | 11.1 | |
| 5 | 11.1 | |
| 6 | 10.6 | |
| 7 | 10.6 | |
| 8 | 10.4 | |
| Mean ± SD | 10.8 ± 0.3 | |
| RSD (%) | 2.7 | |

These results confirm that the method according to the presently disclosed subject matter is accurate and precise, and that the device can be used to accurately measure clottable fibrinogen concentration.

The invention claimed is:

1. A device for performing an in-situ preparation of a sample, said preparation comprising a number of steps and involving at least two substances, the device comprising:
a plurality of substance receiving portions having a top and a bottom, said substance receiving portions have dimensions such that the portions are sufficient to receive therein through the top a predetermined amount of material required for each of said number of steps, wherein said plurality of substance receiving portions constitute an array of wells;
a membrane having an upper surface constituting the bottom of the substance receiving portions and facing towards an interior of the substance receiving portions, and a lower surface facing towards an exterior of the substance receiving portions, and having such a structure as to allow fluid disposed in the substance receiving portions at least in one of the steps, to be transferred therefrom through the membrane towards the exterior of the substance receiving portions only when vacuum is applied to the bottom of the substance receiving portions; and
a plurality of blocking members, each of said members being configured for taking first positions relative to the corresponding substance receiving portions, in which the first positions are disposed in close proximity to the lower surface of the membrane and covers it so as to prevent the possibility of fluid communication between the substance receiving portions and the exterior of the substance receiving portions through the membrane, and second positions spaced away from the membrane, so as to allow said fluid communication when vacuum is applied to the bottom of the substance receiving portions, wherein said device constitutes a part of a system comprising:
an upper plate having an upper surface, a lower surface and a plurality of first well portions extending therebetween, each having a top open end at the upper surface and a bottom open end at the lower surface, each first well portion constituting the corresponding substance receiving portion; and
a membrane sheet configured to be assembled with the upper plate at its lower surface so that an area of the membrane closest to the lower open end of each first well portion and corresponding thereto in shape and dimension constitutes a bottom of the first well portion, and wherein the system further comprises a blocking base with the blocking members each having a blocking flange corresponding in shape and dimension to said area of the membrane.

2. A device according to claim 1, further comprising an elongated cavity with upper and lower openings, a first cavity portion constituted by said substance receiving portion, and a second cavity portion extending between said membrane and the lower opening of the cavity, and wherein said blocking member is insertable into the second cavity portion from the lower open end of the device.

3. A device according to claim 1, wherein at least a part of the device surrounding the substance receiving portion, the membrane and the blocking member are resistant to alkaline substances.

4. A device according to claim 1, wherein the membrane is made of a material, which is at least before use free of absorption properties at least with respect to said substances; is a porous hydrophobic material and/or is inert to at least said substances.

5. A device according to claim 4, wherein said material has pores of a size in the range of 10 to 40 μm.

6. A device according to claim 1, wherein the device is configured for being mounted on a vacuum manifold when the blocking member is spaced away from the membrane so as to allow application of vacuum to the lower surface of the membrane.

7. A device according to claim 2, wherein said blocking member has an extension along the axis (X), which is at least not less than an extension of the second cavity portion along this axis.

8. A device according to claim 1, wherein said system further comprises a sealing arrangement for forming a seal around said area of the membrane and the corresponding lower open end of the first well portion.

9. A device according to claim 1, wherein said system further comprises a lower plate having an upper surface, a lower surface and a plurality of second well portions extending therebetween and having cross-sectional shape and dimension corresponding to those of the first well portions, each second well portion having a top open end at the upper surface of the lower plate and a bottom open end at the lower surface of the lower plate; the upper and lower plates being configured for securing to each other with the membrane sandwiched therebetween so that each pair of corresponding first and the second well portions is coaxially aligned to form one well and are separated by said area of the membrane.

10. A device according to claim 9, wherein said system further comprises a sealing arrangement forming a seal around said area of the membrane and the top open end of the second well portion.

11. A device according to claim 10, wherein one of the first and second plates comprises locks for securely holding together the upper and lower plates, the membrane and the upper and lower sealing sheets forming thereby an assembly with open-ended wells.

12. A device according to claim 1, wherein said blocking members are in the form of a plurality of posts protruding from the blocking base's upper surface, said blocking surfaces being constituted by top surfaces of the posts.

13. A device according to claim 1, wherein the system comprises locks for securely holding the blocking base in fixed relation relative to the upper and lower plates, when the blocking member is in close proximity to the membrane.

14. A device according to claim 11, wherein said assembly is configured for being mounted on a vacuum manifold so that the bottom open ends of the second well portions are exposed for applying vacuum thereto, when said blocking members are spaced away from the membrane.

* * * * *